(12) United States Patent
Franklin

(10) Patent No.: US 7,057,386 B1
(45) Date of Patent: *Jun. 6, 2006

(54) SYSTEM FOR DETECTING METAL CONTENT ON A SEMICONDUCTOR SURFACE AND METHOD OF OPERATING THE SAME

(75) Inventor: Angela G. Franklin, Colleyville, TX (US)

(73) Assignee: National Semiconductor Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/027,774

(22) Filed: Dec. 31, 2004

Related U.S. Application Data

(63) Continuation of application No. 10/349,650, filed on Jan. 23, 2003, now Pat. No. 6,838,874.

(51) Int. Cl.
*G01R 33/12* (2006.01)
*G01N 27/72* (2006.01)

(52) U.S. Cl. .................... 324/228; 324/239; 324/260

(58) Field of Classification Search ........ 324/239–244, 324/256–258, 228, 66, 260, 654, 656–657; 73/DIG. 2, DIG. 3
See application file for complete search history.

(56) References Cited

U.S. PATENT DOCUMENTS

| 5,726,628 A | 3/1998 | Yoo |
| 6,407,546 B1 * | 6/2002 | Le et al. ...................... 324/230 |
| 6,456,079 B1 | 9/2002 | Ott et al. |
| 6,683,452 B1 | 1/2004 | Lee et al. |
| 2004/0155667 A1 * | 8/2004 | Kesil et al. ................. 324/663 |

* cited by examiner

*Primary Examiner*—Bot Ledynh

(57) ABSTRACT

An apparatus for detecting the presence of metal material in a semiconductor wafer. The apparatus comprises: (i) a current-carrying coil for generating a first magnetic field, wherein the first magnetic field is capable of causing the metal material in the semiconductor wafer to generate an opposing magnetic field; and (ii) a detection circuit for detecting the opposing magnetic field generated by the metal material when the semiconductor wafer is in proximity to the current-carrying coil.

20 Claims, 4 Drawing Sheets

SYSTEM FOR DETECTING METAL CONTENT ON A SEMICONDUCTOR SURFACE AND METHOD OF OPERATING THE SAME

This application is a continuation of prior U.S. patent application Ser. No. 10/349,650 filed on Jan. 23, 2003.

TECHNICAL FIELD OF THE INVENTION

The present invention is generally directed to the field of semiconductor wafer manufacturing, and more specifically to systems for detecting metal content on a semiconductor surface and method of operating the same.

BACKGROUND OF THE INVENTION

Semiconductor wafer manufacturing processes are complex and include a plethora of processing steps. These processing steps are, during each of the sequences that are executed as part of the step, closely monitored and may result in a complex web of rework, rejects, partial rework, etc. This invariably results in many diverse flows of partially completed wafers, as opposed to the ideal processing sequence where a wafer proceeds from known step to known step.

Wafers may repeat prior process steps causing concerns of wafers downstream in the processing line to be contaminated with wafers that have already undergone more advanced steps of processing.

It is appropriately important to screen for such occurrences and to limit or eliminate the impact of contamination that may be introduced into a wafer processing operation by wafers that are not part of the regular wafer process flow.

During normal wafer processing, meticulous attention is paid to maintaining a clean, particle free environment. This clean environment has a direct impact on wafer yield and cost. Wafer processing by its very nature tends to introduce impurities into the processing environment; these impurities can for instance be introduced from wafer processing furnaces, by way of example.

In point of fact, particles may diffuse into the semiconductor substrate, especially in areas of the manufacturing process where high frequency operations are being performed on the substrate. This can have a severe detrimental effect on wafer properties making these wafers unsuitable for further use.

In other cases, donor or acceptor dopants may be introduced to substrates. These dopants can have a direct affect on the performance of the devices that are at a later stage to be created from these wafers. Alternatively, other impurities can cause surface defects in the wafer or stacking faults or dislocations in the atomic structure of the substrate. For instance, poor wafer surface can be caused by organic matter that is present in the wafer-processing environment, such as oil or oil related matter.

All possible impurities must be carefully monitored and controlled and must, when present, be removed from the wafer processing environment. This control must be exercised within the cycle of wafer processing steps and at the beginning of the wafer manufacturing process.

The frequency and intensity of such contaminant control operations is highly cost dependent and should, wherever possible, be performed at as low a cost as can be accomplished. Methods of identification and elimination must therefore be simple but effective. Processing conditions and environments can lead to the introduction of a large number of contaminants and therefore lead to the need for strict control of the environment and the way in which the wafers that are being processed are being routed.

Among the contaminants that can accumulate on the surface of a substrate are metals, such as copper, aluminum or the like. Control mechanisms that enhance the monitoring of the level of metal deposited on the surface of a wafer prevent unnecessary re-routing and rework of such wafers. Production cost of semiconductor wafers will be reduced if such wafers can be identified so that only wafers that need to be rerouted for rework are entered into the rework cycle.

There is therefore a need in the art for a system for detecting metal content of a semiconductor surface and method for operating the same, particularly, to detect deposited or sputtered metal layers on all forms of wafer substrates.

SUMMARY OF THE INVENTION

To address the above-discussed deficiencies of the prior art, it is a primary object of the present invention to provide an apparatus for detecting the presence of metal material in a semiconductor wafer. According to an advantageous embodiment of the present invention, the apparatus includes (i) a current-carrying coil for generating a first magnetic field, wherein the first magnetic field is capable of causing the metal material in the semiconductor wafer to generate an opposing magnetic field; and (ii) a detection circuit for detecting the opposing magnetic field generated by the metal material when the semiconductor wafer is in proximity to the current-carrying coil.

According to various advantageous embodiments of the present invention, the apparatus may be associated with a housing, wherein the housing is operable to receive the semiconductor wafer. For instance, the apparatus may suitably be associated with at least one of a sidewall, a bottom wall or a top wall of the housing. According to alternate embodiments, the apparatus may be associated with a portable device, whether wired or wireless, that may be moved into close proximity of the semiconductor wafer under consideration.

Another primary object of the present invention is to provide a method of detecting the presence of metal material in a semiconductor wafer. The method includes the steps of: (i) generating a first magnetic field using a current-carrying coil, wherein the first magnetic field is capable of causing the metal material in the semiconductor wafer to generate an opposing magnetic field; (ii) bringing the semiconductor wafer in proximity to the current-carrying coil; and (iii) detecting the opposing magnetic field generated by the metal material when the semiconductor wafer is in proximity to the current-carrying coil.

According to a related embodiment, in response to detecting the opposing magnetic field, the method further includes the step to generate indicia indicating that metal material is present on a semiconductor wafer.

In an alternate embodiment, it may be possible to determine whether the detected metal is within an acceptable tolerance level. Preferably, such tolerance indicia is compared with at least one threshold, possibly associated with one or more characteristics of the semiconductor wafer, a type of semiconductor wafer, or a use of the semiconductor wafer, whether intended or otherwise. In response to such comparison, the method may further include the step of initiating an alarm event, communicating such tolerance indicia to a monitoring controller, generating statistics, or the like.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the terms "controller" and "processor" may be used interchangeably and mean any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present invention and its advantages, reference is now made to the following description taken in conjunction with the accompanying drawings, in which like reference numerals represent like parts.

DETAILED DESCRIPTION OF THE INVENTION

FIGS. 1 through 5, discussed below, and the various embodiments used to describe the principles of the present invention in this patent document are by way of illustration only and should not be construed in any way to limit the scope of the invention. Those skilled in the art will understand that the principles of the present invention may be implemented in any suitably arranged apparatus for detecting metal content on a semiconductor surface or method of operating the same.

Figure 1A:
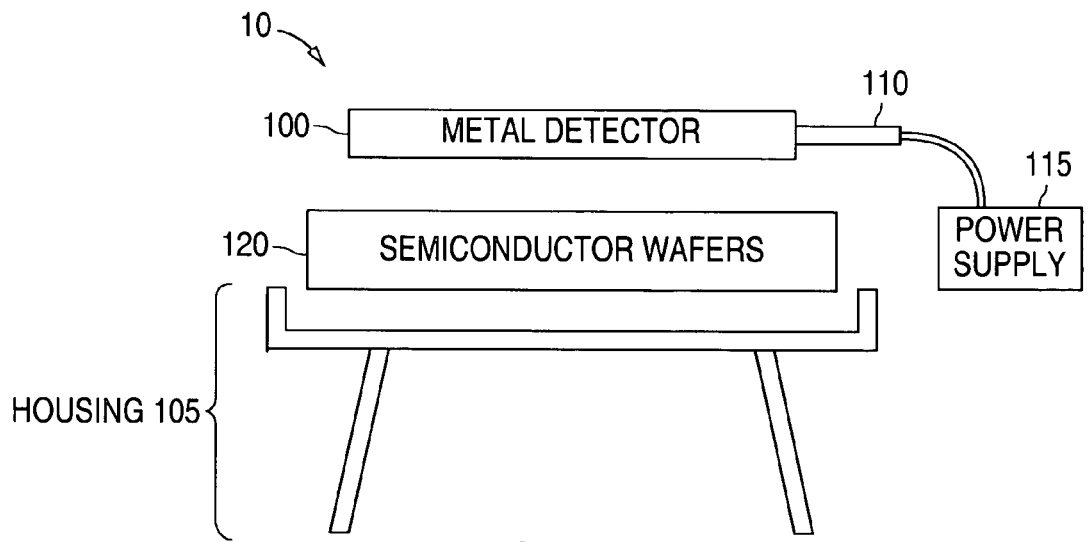
FIG. 1A illustrates a block diagram of an exemplary embodiment of an apparatus for detecting the presence of metal material in a semiconductor wafer according to the principles of the present invention.

Turning initially to FIG. 1A, illustrated is a block diagram of an exemplary embodiment of an apparatus (generally designated 10) for detecting the presence of metal material in one or more semiconductor wafers 120 according to the principles of the present invention. Apparatus 10 comprises a metal detector 100, a housing 105, a stabilizing handle 110 and a power supply 115.

Figure 2A:
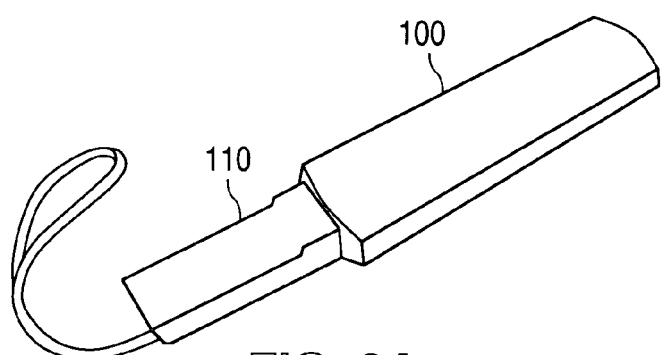
FIG. 2A illustrates an exemplary commercially available handheld security-scanning device that may be used as an apparatus for detecting the presence of metal material in a semiconductor wafer according to the principles of the present invention.
Figure 2B:
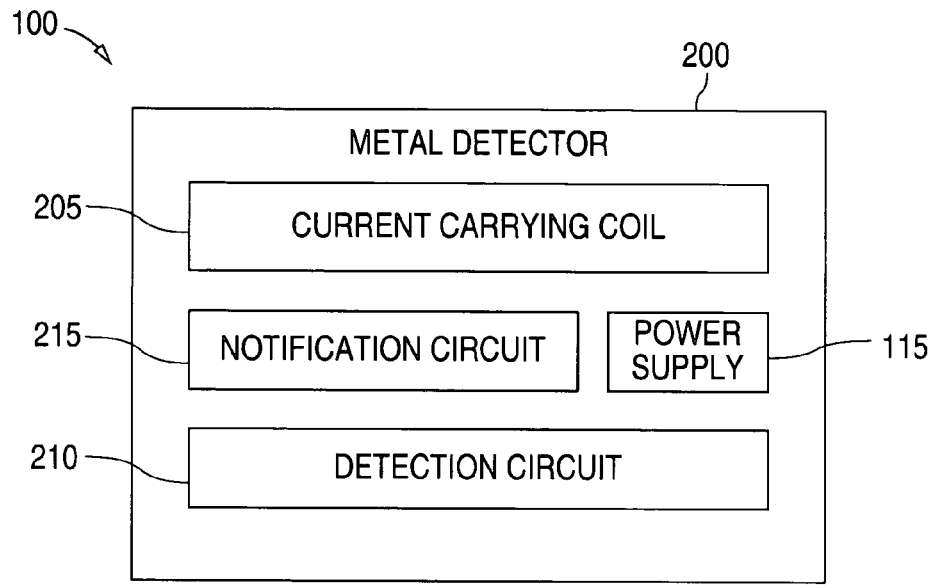
FIG. 2B illustrates an exemplary block diagram of an apparatus for detecting the presence of metal material in a semiconductor wafer according to the principles of the present invention.

Exemplary metal detector 100 includes a current-carrying coil and a detection circuit (both shown with reference to FIG. 2B). The current-carrying coil operates to generate a magnetic field that is capable of causing any metal material present in semiconductor wafers 120 to generate an opposing magnetic field. The detection circuit operates to detect any opposing magnetic field generated by any metal material present when the semiconductor wafers 120 are in proximity to the current-carrying coil.

Exemplary housing 105 is illustrated as a tray for holding the semiconductor wafers 120. For the purposes of this patent document, the term "housing" may be defined broadly as anything that covers, protects, supports, ensconces, holds or otherwise positions the semiconductor wafers 120 for metal material detection as set forth herein, including for instance any frame, bracket, box or the like, whether portable or stationary, and whether including movable parts or not.

Metal detector 100 is a handheld device that is associated with exemplary stabilizing handle 110 and power supply 115. Stabilizing handle 110 steadies metal detector 100 as it sweeps over semiconductor wafers 120. Power supply 115 is illustratively external to metal detector 100 and operates to provide power thereto (according to alternate embodiments, power supply 115 may suitably be disposed within or otherwise associated with metal detector 100 or stabilizing handle 110). Metal detector 100 may be arranged to receive alternating current ("AC") or direct current ("DC").

Figure 1B:
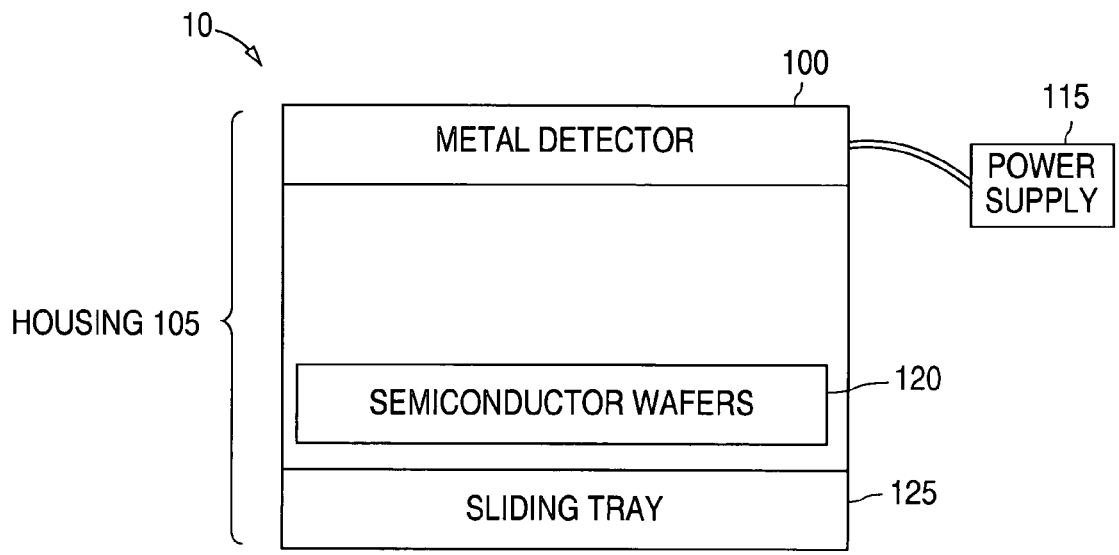
FIG. 1B illustrates an alternate exemplary embodiment of an apparatus for detecting the presence of metal material in a semiconductor wafer according to the principles of the present invention.

Turning next to FIG. 1B, illustrated is an alternate exemplary embodiment of apparatus 10 for detecting the presence of metal material in semiconductor wafers 120 according to the principles of the present invention. Apparatus 10 comprises a metal detector 100 that is illustratively disposed in a top wall of a housing 105, a power supply 115 and a sliding tray 125.

Exemplary metal detector 100 again includes a current-carrying coil and a detection circuit (both shown with reference to FIG. 2B), which operate as described above. Advantageously, metal detector 100 is associated with housing 105, and although shown as disposed in a top wall thereof, may be associated with housing 105 in any manner suitable for detection of metal material. In this embodiment, housing 105 is operable to receive the semiconductor wafers 120 in sliding tray 125. Other exemplary dispositions of metal detector 100 may be in at least one of a sidewall or a bottom wall of housing 105.

It should be noted that the prior-introduced embodiment of FIG. 1A tends not to be as conducive to a semiconductor-manufacturing environment as the present integrated-housing embodiment that allows for a scanning angle critical for optimum metal-film detection, as metal films may only be several microns thick. Again, housing 105 (here in cooperation with sliding tray 125) holds the semiconductor wafers 120.

Turning to FIG. 2A, illustrated is an exemplary commercially available handheld scanning device 100 developed for security purposes that may be used as an apparatus for detecting the presence of metal material in one or more semiconductor wafers 120 according to the principles of the present invention. Exemplary scanning device 100 illustratively includes stabilizing handle 110 and suitably arranged current-carrying coil and detection circuit (both as above-described and shown with reference to FIG. 2B).

Turning next to FIG. 2B, illustrated is an exemplary block diagram of an apparatus 100 for detecting the presence of metal material in one or more semiconductor wafers 120 according to the principles of the present invention. Exemplary apparatus 100 illustratively includes a housing 200 that at least substantially ensconces a current carrying coil 205, a detection circuit 210, a notification circuit 215 and a power supply 115.

Exemplary current carrying coil 205 operates to generate a first magnetic field that is capable of causing any metal material associated with any of semiconductor wafers 120 to generate an opposing magnetic field. Exemplary detection circuit 210 operates to detect the opposing magnetic field generated by the metal material when the semiconductor wafer is in proximity to the current-carrying coil. When current flows through a coil in close proximity to a conducting surface the magnetic field of the coil induces circulating (or "eddy") currents in that surface of the semiconductor wafer 120. The magnitude and phase of the eddy currents will affect the loading on the coil and thus its impedance.

In operation, for example, the flat shape and organized structure of a silicone wafer 120 once it is doped provide optimal conditions for the formation of eddy currents. When scanning doped semiconductor wafers 120, metal detector 100 senses the presence of metal materials by detecting the opposing magnetic field.

Exemplary notification circuit 215, in response to detecting the opposing magnetic field, operates to generate indicia indicating that metal material is present on a semiconductor wafer 120. In alternate embodiments, it may be possible to arrange notification circuit 215 to determine whether the detected metal is within a tolerance level—meaning acceptable or not. Such indicia may be compared with at least one threshold, possibly associated with one or more characteristics of the semiconductor wafer under consideration, a type of semiconductor wafer, or a use of the semiconductor wafer, whether intended or otherwise. In response to such comparison, notification circuit 215 may initiate an alert signal or alarm event (eg., generate an audio indicator (e.g., beep, buzz, etc.), a visual indicator (e.g., LED indicator, etc.), a touch-sensitive indicator (e.g., vibration, etc.) corresponding to a drop in impedance caused by eddy currents sensed), communicate such tolerance indicia to a monitoring controller (shown with reference to FIGS. 4 and 5), generate statistical information or any other data concerning the same, or the like.

Figure 3:
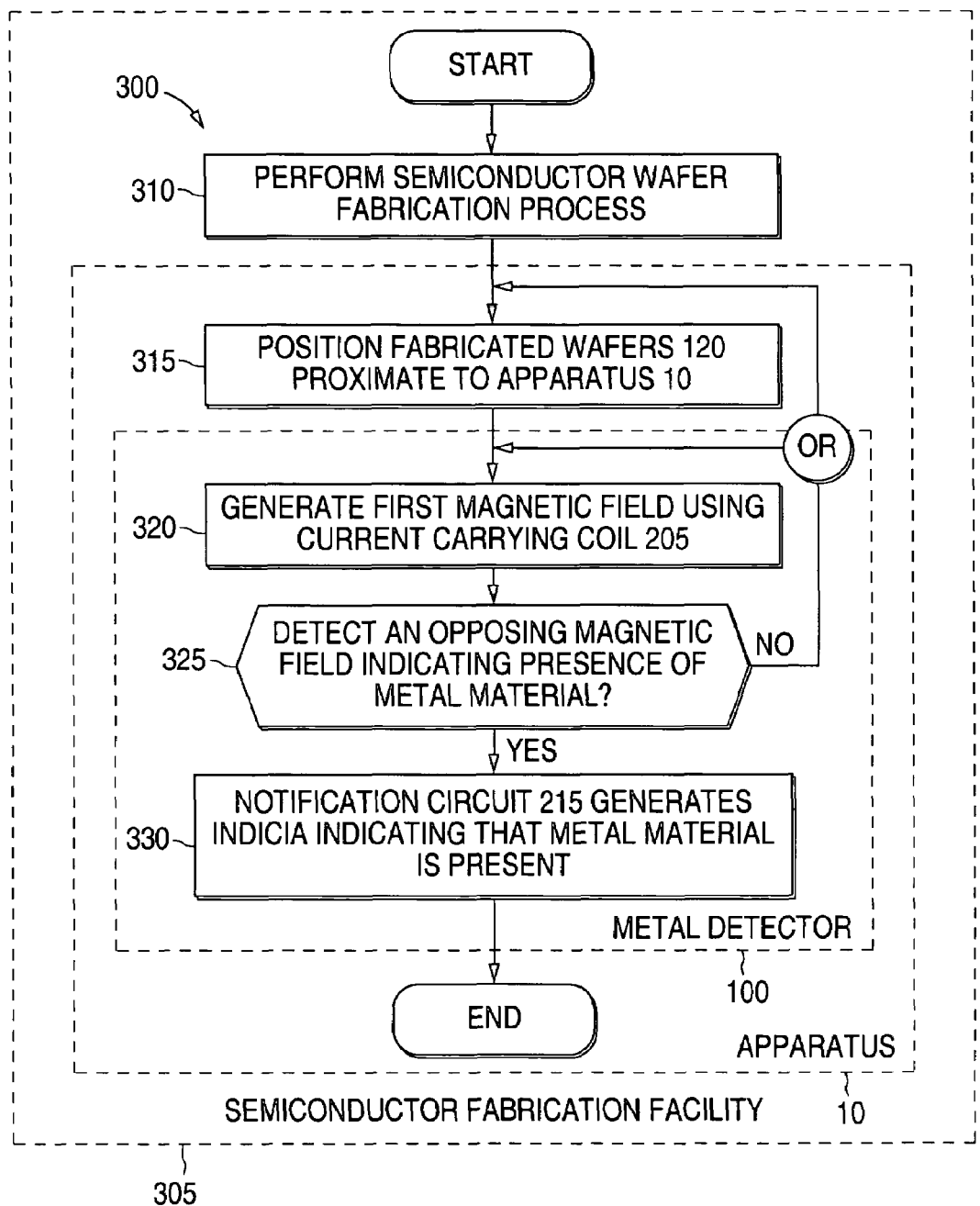
FIG. 3 illustrates an exemplary flow diagram for operating an apparatus for detecting the presence of metal material in a semiconductor wafer according to the principles of the present invention, such as any apparatus disclosed with reference to FIGS. 1 through 2.

Turning to FIG. 3, illustrated is an exemplary flow diagram (generally designated 300) for operating apparatus 10 for detecting the presence of metal material in at least one semiconductor wafer 120 according to the principles of the present invention. For purposes of illustration, concurrent reference is made to apparatus 10 of FIGS. 1 to 2.

To begin, a semiconductor fabrication facility 305 operates a plurality of conventional wafer processing devices (not shown), each of which is capable of performing at least one wafer fabrication process (process step 310). The wafer processing devices fabricate semiconductor wafers 120.

Ones of semiconductor wafers 120 are positioned in association with (or in association with means for positioning the semiconductor wafers 120) an apparatus 10 for detecting the presence of metal material therein (process step 315). Apparatus 10 generates a first magnetic field using a current-carrying coil 205, wherein the first magnetic field is capable of causing metal material in any of the ones of semiconductor wafers 120 to generate an opposing magnetic field (process step 320). Apparatus 10 and one or more semiconductor wafers 120 under examination are brought in suitable proximity with respect to one another and detection circuit 210 operates to detect any opposing magnetic field generated if any metal material is present on any of semiconductor wafers 120 (decision step 325).

In response to detecting the opposing magnetic field ("YES" branch of decision step 325), notification circuit 215 generates indicia indicating that metal material is present on a semiconductor wafer 120 (process step 330).

In an alternate embodiment, it may be possible to arrange notification circuit 215 to determine whether the detected metal is within a tolerance level. Such indicia may be compared with at least one threshold, possibly associated with one or more characteristics of the semiconductor wafer, a type of semiconductor wafer, or a use of the semiconductor wafer, whether intended or otherwise. In response to such comparison, notification circuit 215 may similarly initiate the alert signal or alarm event, communicate such tolerance indicia to a monitoring controller (shown with reference to FIGS. 4 and 5), generate statistical information or any other data concerning the same, or the like.

Figure 4:
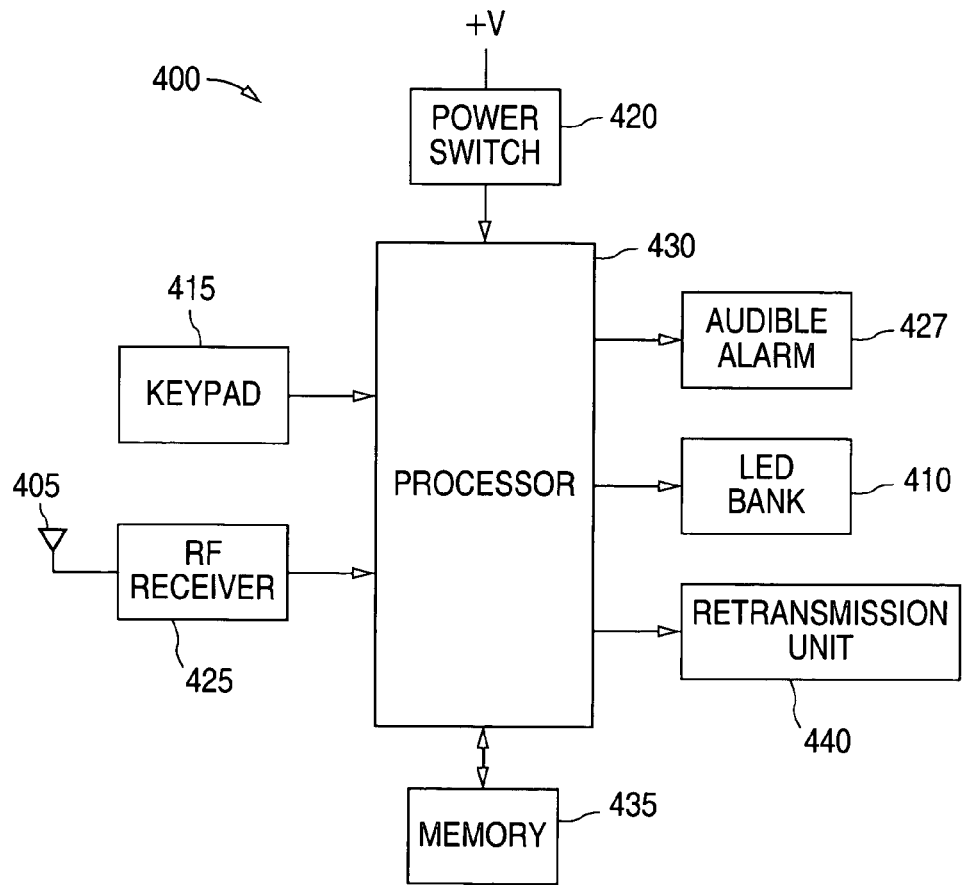
FIG. 4 illustrates a block diagram of an exemplary remote receiver unit of the system of the present invention.

Turning to FIG. 4, illustrated is a block diagram of an exemplary remote receiver unit (generally designated 400) of a system of the present invention. In a distributed system in accord with one embodiment of this invention, unit 400 (e.g., a wall-mountable unit) is provided for receipt of transmissions from at least one apparatus 10 (which may be associated with a suitably arranged transmitter, and whereby any suitable means of communication may be used between unit 400 and apparatus 10).

Exemplary unit 400 illustratively includes a receiver antenna 405, indicator LED's 410 (e.g., including indicators for as many detector functions as are employed in the specific embodiment of apparatus 10 being monitored, as well as an indicator for unit on/off status), and a user interface input keypad 415 for unit setup, reset and alarm deactivation. Power access is also provided at switch 420.

Exemplary RF receiver 425 operates to receive indicia signal transmissions, such as, for instance, an alert signal or alarm event 427, statistical information or any other data concerning the same, or the like. Receiver 425 communicates received signals to processor 430 for identification and appropriate output. Processor 430 also receives inputs from keypad 415 and power switch 420. Exemplary non-volatile memory 435 is provided for input of identification of the user or of apparatus 10 being monitored. Audible alarm 427, LED bank 410 and retransmission unit 440 (e.g., auto-dialer, imbedded digital wireless technology, RF transmitter or the like) are connected to receive outputs from processor 430.

In exemplary operation, when a transmission is received, including when power at apparatus 10 is low, an alarm may be sounded and the appropriate LED (e.g., indicative of the condition causing the alarm event, for example a malfunction of apparatus 10, sensing of metal material in semiconductor wafers 120, etc.) is activated. If not disabled by the user at apparatus 10 within a short period of time, processor 430 activates retransmission unit 440 initiating a call for help or other remote notification (as discussed with reference to FIG. 5).

Operational setup of unit 400 is also accomplished under programming at processor 430 and by sequential operation by a user or technician of keypad 415 (including user ID set, learn mode operations, reset or reprogramming operations, urgency code operations, and the like).

Figure 5:
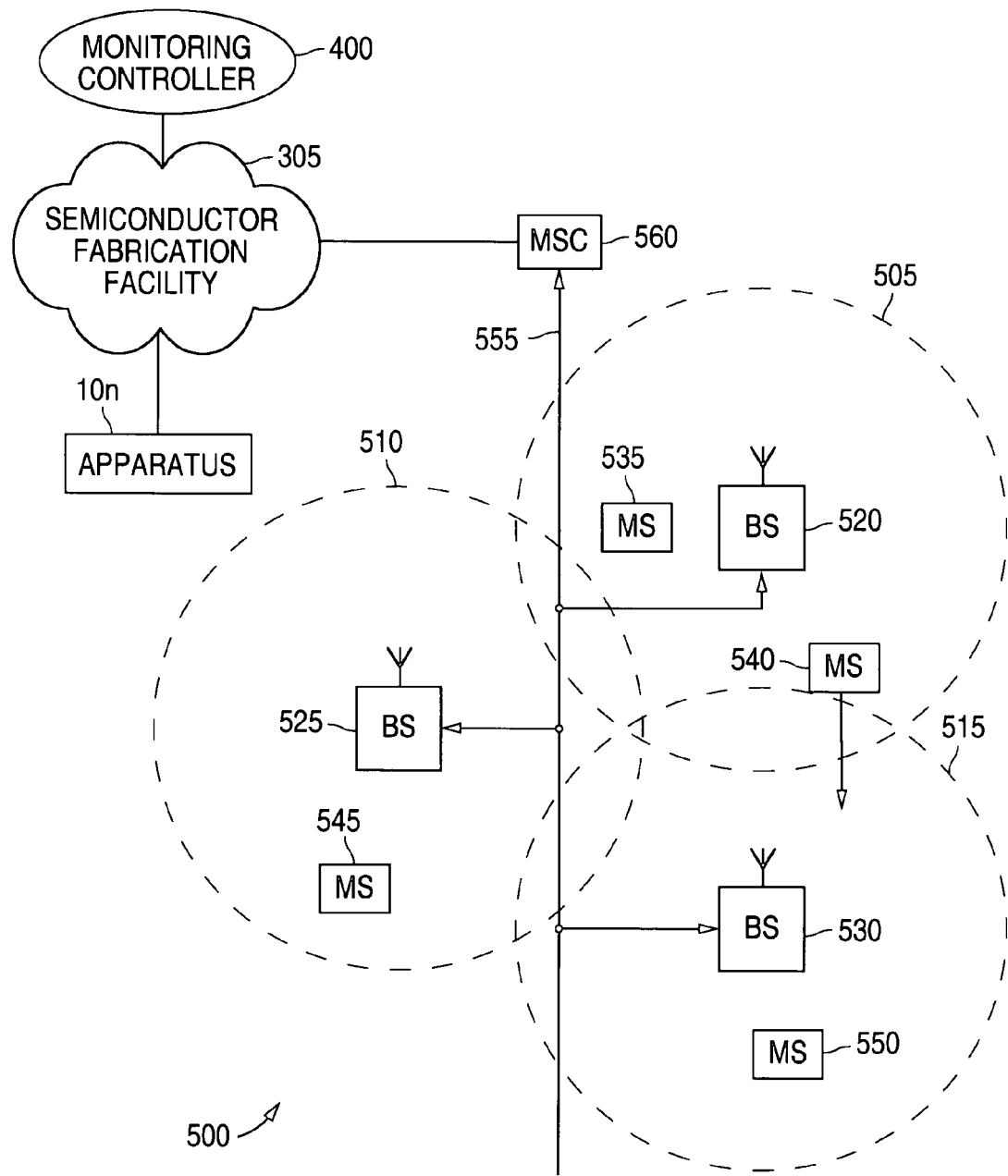
FIG. 5 illustrates an exemplary hybrid wireless/wired network that is associated with a remote monitoring controller according to one embodiment of the present invention.

Turning lastly to FIG. 5, illustrated is an exemplary hybrid wireless/wired network (generally designated 500) that is associated with a remote monitoring controller (unit 400) according to one embodiment of the present invention. Exemplary network 500 is introduced for illustrative purposes only, and comprises a plurality of cell sites 505 to 515, each containing one of the base stations ("BS") 520 to 530. Base stations 520 to 530 are operable to communicate with a plurality of mobile stations ("MS") 535 to 550. MS 535 to 550 may be any suitable cellular devices, including conventional cellular telephones, PCS handset devices, portable computers, metering devices, transceivers, and the like.

Dotted lines show the approximate boundaries of the cell sites 505 to 515 in which BS 520 to 530 are located. The cell sites are shown approximately circular for the purposes of illustration and explanation only. It should be clearly understood that the cell sites also may have irregular shapes, depending on the cell configuration selected and natural and man-made obstructions, and may be part of an intranet or an extranet, or both, as the case may be. Alternatively, the network may suitably be wired, at least in part.

In one embodiment of the present invention, BS 520 to 530 may comprise a base station controller ("BSC") and a base transceiver station ("BTS"). BSC and BTS are well known to those skilled in the art. A BSC is a device that manages wireless communications resources, including the BTS, for specified cells within a wireless communications network. A BTS comprises the RF transceivers, antennas, and other electrical equipment located in each cell site. This equipment may include air conditioning units, heating units, electrical supplies, telephone line interfaces, and RF transmitters and RF receivers, as well as call processing circuitry. For the purpose of simplicity and clarity in explaining the operation of the present invention, the BTS in each of cells 505 to 515 and the BSC associated with each BTS are collectively represented by BS 520 to 530, respectively.

BS 520 to 530 may transfer voice or data signals between each other and, possibly, a public telephone system (not shown) via communications line 555 and mobile switching center ("MSC") 560. MSC 560 is well known to those skilled in the art, and is a switching device that provides services and coordination between the subscribers in a wireless network and external networks, such as the Internet, public telephone system, etc. Communications line 555 may be any suitable connection means, including a T1 line, a T3 line, a fiber optic link, a network backbone connection, and the like. In some embodiments of the present invention, communications line 555 may be several different data links, where each data link couples one of BS 520 to 530 to MSC 560.

In the exemplary wireless network 500, MS 535 is located in cell site 505 and is in communication with BS 520, MS 545 is located in cell site 510 and is in communication with BS 525, and MS 550 is located in cell site 515 and is in communication with BS 530. MS 540 is also located in cell site 505, close to the edge of cell site 515. The direction arrow proximate MS 540 indicates the movement of MS 540 towards cell site 515 and a communications handoff thereto.

For the purposes of illustration, it is assumed that unit 400 receives indicia signals, including possibly alert signals or alarm events, statistical information or any other data concerning the same, or the like. In response to application dependent programming at unit 400 for semiconductor fabrication facility 305 for metal material detection in semiconductor wafers 120, supervisors or management, whether human or machine, may be communicated information concerning such indicia signals periodically, or based upon accumulation or relevant priority of such received signals or information related thereto.

For instance, as semiconductor wafers 120 are positioned in association with apparatus 10, and, in response to detecting opposing magnetic fields in an intolerable quantity of wafers 120 (possibly in a particular lot or group of lots), notification circuit 215 generates a "priority" indicia signal indicating that metal material is present in an unacceptable quantity of wafers 120. This signal is communicated from apparatus 10 to unit 400. In response thereto, unit 400 communicates the same via network 500 to MS 540, a mobile communication device controlled by an appropriate fabrication supervisor. The supervisor is informed of the problem expeditiously.

Although the present invention has been described with an exemplary embodiment, various changes and modifications may be suggested to one skilled in the art. It is intended that the present invention encompass such changes and modifications as fall within the scope of the appended claims.

What is claimed is:

1. An apparatus, comprising:
   a current-carrying coil for generating a magnetic field;
   a detection circuit for detecting an opposing magnetic field generated by metal material in a semiconductor wafer in response to the magnetic field; and
   an indicator for generating an indication identifying whether the metal material is present in the semiconductor wafer based on the detected opposing magnetic field.

2. The apparatus of claim 1, further comprising a notification circuit for generating indicia indicating whether the metal material is present in the semiconductor wafer based on the detected opposing magnetic field;
   wherein the indicator generates the indication based on the generated indicia.

3. The apparatus of claim 2, wherein the notification circuit is further capable of determining whether the metal material is present in the semiconductor wafer within a tolerance level.

4. The apparatus of claim 3, wherein the notification circuit is capable of determining whether the metal material is present in the semiconductor wafer within the tolerance level by comparing the indicia to one or more thresholds.

5. The apparatus of claim 4, wherein the one or more thresholds are based on one or more characteristics of the semiconductor wafer.

6. The apparatus of claim 4, wherein the one or more thresholds are based on a type of semiconductor wafer.

7. The apparatus of claim 4, wherein the one or more thresholds are based on an intended use of the semiconductor wafer.

8. The apparatus of claim 3, wherein the notification circuit is capable of causing the indicator to generate the indication when:
the metal material is present in the semiconductor wafer within the tolerance level; or
the metal material is present in the semiconductor wafer outside of the tolerance level.

9. The apparatus of claim 2, wherein the notification circuit is further capable of at least one of:
communicating at least one of an alert signal, an alarm event, and the generated indicia to a monitoring controller; and
generating statistical information associated with the detected opposing magnetic field.

10. The apparatus of claim 1, wherein the indicator comprises one or more of: a visual indicator, an audio indicator, and a touch-sensitive indicator.

11. The apparatus of claim 1, further comprising:
a power supply for supplying power to the current-carrying coil and the detection circuit; and
a housing for holding the current-carrying coil and the detection circuit.

12. The apparatus of claim 11, further comprising one of:
a sliding tray for inserting the semiconductor wafer into the housing; and
a stabilizing handle for allowing an operator to move the housing near the semiconductor wafer.

13. The apparatus of claim 1, wherein the detection circuit detects a change in impedance that varies based on currents in the metal material in the semiconductor wafer.

14. A method, comprising:
generating a magnetic field;
detecting an opposing magnetic field generated by metal material in a semiconductor wafer in response to the magnetic field; and
generating an indication identifying whether the metal material is present in the semiconductor wafer based on the detected opposing magnetic field.

15. The method of claim 14, further comprising generating indicia indicating whether the metal material is present in the semiconductor wafer based on the detected opposing magnetic field;
wherein generating the indication comprises generating the indication based on the generated indicia.

16. The method of claim 15, further comprising determining whether the metal material is present in the semiconductor wafer within a tolerance level by comparing the indicia to one or more thresholds; and
wherein generating the indication comprises generating the indication when:
the metal material is present in the semiconductor wafer within the tolerance level; or
the metal material is present in the semiconductor wafer outside of the tolerance level.

17. The method of claim 16, wherein the one or more thresholds are based on at least one of: one or more characteristics of the semiconductor wafer, a type of semiconductor wafer, and an intended use of the semiconductor wafer.

18. The method of claim 15, further comprising:
communicating at least one of an alert signal, an alarm event, and the generated indicia to a monitoring controller; and
generating statistical information associated with the detected opposing magnetic field.

19. A facility, comprising:
one or more wafer processing devices each capable of performing at least one wafer fabrication process; and
an apparatus, comprising:
a current-carrying coil for generating a magnetic field;
a detection circuit for detecting an opposing magnetic field generated by metal material in a semiconductor wafer in response to the magnetic field; and
an indicator for generating an indication identifying whether the metal material is present in the semiconductor wafer based on the detected opposing magnetic field.

20. The facility of claim 19, wherein the apparatus further comprises a notification circuit for generating indicia indicating whether the metal material is present in the semiconductor wafer based on the detected opposing magnetic field;
wherein the indicator generates the indication based on the generated indicia.

* * * * *